United States Patent
D'Agostino et al.

(10) Patent No.: US 12,310,938 B2
(45) Date of Patent: *May 27, 2025

(54) COMPOSITIONS AND METHODS FOR WEIGHT LOSS MAINTENANCE

(71) Applicant: UNIVERSITY OF SOUTH FLORIDA, Tampa, FL (US)

(72) Inventors: Dominic Paul D'Agostino, Tampa, FL (US); Angela Marie Poff, Tampa, FL (US); Andrew Paul Koutnik, Tallahassee, FL (US)

(73) Assignee: University of South Florida, Tampa, FL (US)

( * ) Notice: Subject to any disclaimer, the term of this patent is extended or adjusted under 35 U.S.C. 154(b) by 111 days.

This patent is subject to a terminal disclaimer.

(21) Appl. No.: 18/117,059

(22) Filed: Mar. 3, 2023

(65) Prior Publication Data
US 2023/0285348 A1 Sep. 14, 2023

Related U.S. Application Data

(63) Continuation of application No. 16/772,490, filed as application No. PCT/US2018/065244 on Dec. 12, 2018, now Pat. No. 11,596,616.

(60) Provisional application No. 62/597,640, filed on Dec. 12, 2017, provisional application No. 62/630,492, filed on Feb. 14, 2018.

(51) Int. Cl.
| | |
|---|---|
| *A61K 31/22* | (2006.01) |
| *A23L 33/00* | (2016.01) |
| *A23L 33/10* | (2016.01) |
| *A61K 9/00* | (2006.01) |
| *A61K 31/19* | (2006.01) |
| *A61P 3/04* | (2006.01) |

(52) U.S. Cl.
CPC .............. *A61K 31/22* (2013.01); *A23L 33/10* (2016.08); *A23L 33/30* (2016.08); *A61K 9/0056* (2013.01); *A61K 31/19* (2013.01); *A61P 3/04* (2018.01); *A23V 2002/00* (2013.01)

(58) Field of Classification Search
CPC ............ A61K 31/22; A61K 31/19; A61P 3/04
See application file for complete search history.

(56) References Cited

U.S. PATENT DOCUMENTS

| | | | | |
|---|---|---|---|---|
| 10,646,462 | B2 * | 5/2020 | D'Agostino | ......... A61K 31/047 |
| 11,596,616 | B2 * | 3/2023 | D'Agostino | ......... A61K 9/0056 |
| 2014/0350105 | A1 | 11/2014 | D'Agostino | |
| 2016/0317487 | A1 | 11/2016 | D'Agostino et al. | |
| 2017/0000754 | A1 | 1/2017 | Weeber et al. | |
| 2017/0172969 | A1 | 6/2017 | D'Agostino | |
| 2017/0266148 | A1 | 9/2017 | D'Agostino et al. | |
| 2018/0213833 | A1 | 8/2018 | Gupta | |

FOREIGN PATENT DOCUMENTS

| | | | | |
|---|---|---|---|---|
| EP | 0318357 | A2 | 5/1989 | |
| WO | WO-2014153416 | A1 * | 9/2014 | ............... A23L 2/52 |
| WO | WO-2015156865 | A1 * | 10/2015 | ............. A61K 31/22 |

OTHER PUBLICATIONS

International Search Report and Written Opinion in PCT/US2018/065244. Mailed Mar. 22, 2019. 12 pages.
Wikipedia, "Cellular respiration", Nov. 8, 2017. Retrieved on Feb. 19, 2019 from https://en.wikipedia.org/w/index.php?title=Cellulauespiration&oldid=809379518.
Romsos DR., Butanediol and lipid metabolism. Federation Proceedings [Nov. 1, 1975, 34(12):2186-2190].
Romsos DR., Influence of dietary 1,3 butanediol on weight gain, blood, and liver metabolites and lipogenesis in the pig and chick. Journal of Nutrition. Mar. 1975.
WHO Food Additives Series 14, 467, Butane-1,3-diol. Retrieved from http://www.inchem.org/documents/jecfa/jecmono/v14je03.htm on Nov. 30, 2017.
Scala, R.A. and Paynter, O.E., Chronic oral toxicity of 1,3-butanediol, Toxicology and Applied Pharmacology, 1967, 10, 1:160-164.
Extended European Search Report in PCT/US2018/065244. Mailed Jul. 20, 2021. 9 pages.
Kesl, Shannon L. et al. "Effects of exogenous ketone supplementation on blood ketone, glucose, triglyceride, and lipoprotei levels in Sprague-Dawley rats." Nutrition & Metabolism, vol. 13, No. 9 (2016).
Tashim, Sami A. et al. "Ketone body therapy: from the ketogenic diet to the oral administration of ketone ester." Journal of Lipid Research, vol. 55, No. 9. (2014).
Desrochers, Sylvain et al. "R, S-1, 3-butanediol acetoacetate esters, potential alternatives to lipid emulsions for total parenteral nutrition." The Journal of Nutritional Biochemistry, vol. 6, No. 2 (1995).
Kennedy, Adam R. et al. "A high-fat, ketogenic diet induces a unique metabolic state in mice." American Journal of Physiology: Endocrinology and Metabolism, vol. 292, No. 6 (2007).
Desrochers, S. et al. "Metabolism of (R,S)-1,3-butanediol acetoacetate esters, potential parenteral and enteral nutrients in conscious pigs." American Journal of Physiology: Endocrinology and Metabolism, vol. 268 (1995).
Vandenberghe, Camille, et al. "Caffeine intake increases plasma ketones: an acute metabolic study in humans." Canadian journal of physiology and pharmacology 95.4 (2017): 455-458.

* cited by examiner

*Primary Examiner* — Kevin E Weddington
(74) *Attorney, Agent, or Firm* — Meunier Carlin & Curfman LLC (57) ABSTRACT

Compositions and methods for inducing weight loss, fat loss, maintaining weight or fat loss, suppressing appetite, reducing calorie intake, reducing weight gain, decreasing feed efficiency, increasing metabolic inefficiency, increasing energy expenditure, increasing thermogenesis and/or resetting metabolic set are disclosed. The compositions have a therapeutically effective amount of a ketogenic supplement, e.g., a ketone diesters, such as R,S 1,3-butanediol diacetoacetate. Compositions of one or more beta-hydroxy butyrate, beta-hydroxybutyrate salt, and medium chain triglycerides are also disclosed.

9 Claims, 9 Drawing Sheets

COMPOSITIONS AND METHODS FOR WEIGHT LOSS MAINTENANCE

CROSS REFERENCE TO RELATED APPLICATIONS

This application is a continuation of U.S. application Ser. No. 16/772,490, filed Jun. 12, 2020, which claims the benefit of U.S. National stage application of International Application Number PCT/US2018/065244, filed on Dec. 12, 2018, which claims the benefit of priority to U.S. Provisional Application Nos. 62/597,640, filed Dec. 12, 2017, and 62/630,492, filed Feb. 14, 2018, the disclosures of each are incorporated by reference herein in their entireties.

FIELD

This invention relates, generally, to weight loss and weight loss maintenance. More specifically, it relates to ketone-related methods and compositions for inducing weight loss and maintaining that weight loss long term.

BACKGROUND

Greater than 70% of Americans are overweight or obese with the incidence continuing to rise. Obesity is directly or indirectly involved in at least 5-10 of the leading causes of death. Recently, conforming to a ketogenic diet and/or supplementing with ketogenic compounds has become popular for weight loss. However, sustained benefits of weight loss are only realized as long as weight loss is maintained; weight loss is distinctly different from weight loss maintenance.

Generally, nutritional, or therapeutic, ketosis is the physiological state of elevated blood ketone body levels (typically above 0.5 mmol/L) resulting from ketogenic diets, calorie restriction, therapeutic fasting and/or supplementation with ketogenic precursors. Ketone bodies represent alternative energy substrates for both peripheral tissues and the central nervous system. The two most abundant and physiologically significant ketone bodies are acetoacetate and β-hydroxybutyrate (PHB), while the third ketone body, acetone, is produced as a byproduct that the lungs breathe off. The carbohydrate restriction is typically necessary for the body to produce ketone levels in the therapeutic range 2-7 mM/L.

The body produces ketone bodies during nutritional or therapeutic ketosis in the range of 0.5-8 mmol/L. The metabolism of ketone bodies is associated with anticonvulsant effects, enhanced brain metabolism, neuroprotective, muscle sparing properties and improvement in cognitive and physical performance. Science-based improvements in efficiency of cellular metabolism, managed through ketone supplementation, could have beneficial impacts on physical, cognitive health, psychological health, warfighter resilience and a long-term impact on health with respect to the common avoidable diseases such as obesity, neurodegenerative diseases, diabetes and cancer. Evidence suggests that the health benefits from calorie restriction, ketogenic diet, or dietary restriction may be due to the effect of ketones on gene expression (Shimazu et al. Suppression of oxidative stress by β-hydroxybutyrate, an endogenous histone deacetylase inhibitor. Science. 2013 Jan. 11; 339(6116):211-4), it's anti inflammatory effects by inhibiting NLRP3 inflammasome (Youm et al. 2015; The ketone metabolite β-hydroxybutyrate blocks NLRP3 inflammasome-mediated inflammatory disease. *Nature Medicine*) and binding HCAR2 (Rahman et al. 2014; The β-hydroxybutyrate receptor HCA2 activates a neuroprotective subset of macrophages. *Nature Communications*), and muscle sparing properties.

Under normal conditions of the standard American diet, the brain is almost exclusively dependent upon the metabolism of glucose to supply its metabolic energy. Though the brain is only 2% of bodyweight, it represents 25% of total glucose consumption. Ketones can replace glucose to supply most of the brain's metabolic energy needs (>50%) during periods of limited glucose availability resulting from starvation/fasting, caloric restriction or carbohydrate restriction as in ketogenic diets (Cahill, Jr., Fuel metabolism in starvation. *Annu Rev Nutr* 26: 1-22, 2006). During carbohydrate deprivation, glucose availability decreases causing a metabolic shift towards fatty acid beta-oxidation and the production of ketone bodies for energy homeostasis.

Dietary carbohydrates (carbs) include simple sugars, such as table sugar (sucrose) and complex carbohydrates (starch) found in foods like potatoes and pasta. Carbohydrate and sugar consumption have dramatically increased in the last two centuries in Western societies. When sugars and carbohydrates are consumed by humans, the pancreas secretes insulin, a hormone used to transport glucose into various body tissue, preferentially muscle and fat. The glucose is then used by the body as a fuel source. In most Western diets, glucose is the body's primary fuel source.

In periods of fasting, extreme exercise, and/or low carbohydrate consumption, glucose stores in the body are rapidly used and can become quickly depleted. Failure to replenish glucose stores as they become depleted causes the body to turn to an alternative method to generate energy by creating ketone bodies. Ketone bodies can be used by almost every cell of the body as a replacement fuel to satisfy the body's energy needs, including the needs of the brain. During a prolonged fast, for example, blood ketone levels will increase to as high as 2 or 3 mmol/L. It is conventionally understood and agreed that when blood ketones rise above 0.5 mmol/L, the heart, brain and peripheral tissues are using ketone bodies (beta hydroxybutyrate and acetoacetate) as a primary fuel source. This condition is referred to as ketosis, or "nutritional ketosis." This is distinguished from, and should not be confused with, diabetic or alcoholic ketoacidosis, which is the runaway accumulation of ketone bodies and associated drop in blood pH. Diabetic ketoacidosis is associated with the absence of insulin as occurs in those suffering from type 1 diabetes. Ketoacidosis typically results in blood ketone levels in excess of 20 mmol/L in combination with metabolic derangement and electrolyte imbalance.

When in ketosis, the body essentially burns fat for fuel. This is accomplished because fat stores in the body are utilized to create the water-soluble ketone bodies beta-hydroxybutyrate (βHB) and acetoacetate. These ketone bodies are then used by the body as a primary energy source.

The body enters a state of ketosis when it has no dietary source of glucose or sugar and its stores of glycogen have been depleted. This typically occurs during fasting, exercise, and/or pursuing a carbohydrate restricted ketogenic diet. Upon transitioning into ketosis, the body begins cleaving fats into fatty acids and glycerol and transforms the fatty acids into acetyl CoA molecules which are then eventually transformed into ketone bodies in the liver. In other words, during ketogenic metabolism in the liver, the body uses dietary and bodily fats as its primary energy source. Consequently, once in ketosis, one can easily induce loss of body fat by reducing dietary fat intake and adjusting carbohydrate intake low enough to sustain ketosis.

A ketogenic diet is one that is high in dietary fat and low in carbohydrates with moderate levels of protein (approximately 1-2 g/kg). The classical ketogenic diet consists of a strict regimen of 4 parts fat to 1 part protein+carbohydrate (with the carbohydrate being typically less than 25-50 g per day). It has been suggested that the ideal macronutrient ratio to maintain a ketogenic diet is 65-85 percent of calories from fats, 10-20 percent of calories from proteins, and 5 percent of calories from carbohydrates.

A significant advantage of pursuing weight loss through a ketogenic diet is that a ketogenic diet may result in loss of fat stores while maintaining and protecting muscle mass. Some studies have suggested that the muscle sparing properties of a ketogenic diet result in improvement in physical performance. Athletes who maintain nutritional ketosis maintain lower insulin levels and can better utilize fatty acids and ketones for fuel, effectively sparing blood glucose, which has the potential to optimize and prolongs physical and mental performance. This state is referred to as being "keto adapted." Keto adaptation occurs when the body adjusts to ketosis by building up the necessary fat-burning enzymes, fat oxidation is elevated, serum ketone levels are elevated, hormone levels are changed to accommodate ketosis, and the body is carrying less water.

Individuals on the standard American diet can expect to get peak fat oxidation while exercising from between 60 to 65 percent of their maximum oxygen consumption ($VO_2$ max); higher exertion levels may deplete glycogen stores. Keto-adapted individuals draw proportionally more substrate from fats and ketones (sparing glycogen) and can shift the peak to much higher $VO_2$ levels and thus sustain effort for an extended duration. Transitioning to a keto-adapted state (blood ketones >0.5 mmol/L) typically requires 1 or more weeks (depending on the person) with severe restriction of carbohydrates (<25 g/day) and moderate protein restriction (1 g/kg/day) with the balance of macronutrient from fat. A sustained physiological decrease in glucose and insulin are required for sustained hepatic ketogenesis, which is very difficult for most humans.

Vlahakos (U.S. Pat. No. 6,613,356) provides a weight-loss composition using n-butyrate ions from potassium butyrate or related compounds. Butyric acid stimulates receptors in the stomach that the stomach is full and food is stagnant in the stomach. Thus, consuming butyric acid precursors prior to eating reduces food consumption. Testing showed the compositions improved a patient's ability to withstand rigorous exercise, improved hypercholesterolemia and hypertriglyceridemia, and reduced fatigue.

Another advantage to pursuing weight loss through a ketogenic diet is that being in ketosis reduces hunger. Indeed, hunger is the major barrier that is often cited for the inability to maintain a traditional calorie restricted diet.

Despite the many health advantages to pursuing a ketogenic diet and maintaining a state of nutritional ketosis, there remain significant barriers to pursuing and maintaining a ketogenic lifestyle. One of these barriers is the difficulty of transitioning into a ketogenic state. The fastest way to deplete glucose stores in the body is through fasting combined with exercise. This is physically and emotionally demanding and is an extreme challenge even for the most motivated and disciplined.

In addition, even if nutritional ketosis is obtained and significant weight loss is achieved, there is a major problem with weight loss maintenance, distinct from weight loss itself. It is now accepted within the field that weight loss is distinct from weight loss maintenance (Kraschnewski et al. Long-term weight loss maintenance in the United States. *Int J Obes*. 2010; Hall & Kahan. Maintenance of Lost Weight and Long-Term Management of Obesity. *Med Clin North Am*. 2018). While weight loss can be initially achieved, failure rates of weight loss maintenance in the United States are as high as 95% (Kraschnewski et al. Long-term weight loss maintenance in the United States. Int J Obes. 2010). Only 36.5% of overweight/obese US adults that lose 5% of their bodyweight are capable of maintaining that loss. The success rate drops further after greater degrees of weight loss; for example, only 4.4% of individuals maintain a 20% weight loss.

During initial weight loss, biological changes that attempt to reverse weight loss and inhibit weight loss maintenance accumulate (MacLean et al. Biology's response to dieting: the impetus for weight regain. *Am J Physiol Regul Integr Comp Physiol*. 2011; Trexler et al. Metabolic adaptation to weight loss: implications for the athlete. *J Int Soc Sports Nutr*. 2014). Consequently, individuals who initially lose weight are set up to regain weight, not maintain weight loss. Biologically, when individuals lose weight they undergo a caloric restriction resulting in decreased bodyweight, fat mass, and fat free mass. This causes a decrease in the thermic effect of food and lowers basal metabolic rate. Additionally, leptin and insulin decrease, while ghrelin elevates, to induce hyperphagia, or the desire to overeat. Taken together, individuals who undergo weight loss have reduced energy expenditure, and increased feed and metabolic efficiency, which attempts to causes dieters to get back to their pre-dieting metabolic set-point. Connections have been made previously between ketogenic supplementation and weight loss, examples including US2016/0317487; EP0318357; Romsos D R, et al. Influence of dietary 1,3-butanediol on weight gain, blood, and liver metabolites and lipogenesis in the pig and chick. J Nutr. 1975 February; 105(2):161-70; Reuzel, P. G. J. et al. (1978) Report "Subchronic (13-week) feeding study with 1,3-butanediol in beagle dogs" No. R 5485 by Central Institute for Nutrition and Food Research, submitted to WHO, dated September 1978; and Scala, R. A. et al. (1967) Toxicol. Appl. Pharmacol., 10, 160. However, the conventional art only attempts to induce weight loss and not necessarily maintain that weight loss-very different endeavors.

Accordingly, what is needed is a method and/or composition for inducing and maintaining weight loss. The compositions and methods disclosed herein address these and other needs.

SUMMARY

In accordance with the purposes of the disclosed materials and methods, as embodied and broadly described herein, the disclosed subject matter, in one aspect, relates to weight loss, fat loss, and weight and fat loss maintenance and methods for preventing or treating these conditions. In certain aspects, disclosed are compositions and methods for inducing weight loss, inducing fat loss, and/or maintaining the weight or fat loss. In further aspects, disclosed are compositions and methods for suppressing appetite, reducing calorie intake, or reducing weight gain. In yet further aspects, disclosed are compositions and methods for decreasing feed efficiency, increasing metabolic inefficiency, increasing energy expenditure, increasing thermogenesis and/or resetting metabolic set point. Still further, disclosed are compositions and methods for treating adipose tissue wasting.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

For a fuller understanding of the invention, reference should be made to the following detailed description, taken in connection with the accompanying drawings, in which:

FIGS. 2A-2B depict results of an acute gavage trial in rats. Control: water (5 g/kg once daily; KE: R,S 1,3-butanediol diacetoacetate (5 g/kg once daily); BHB-S: beta-hydroxybutyrate salt (5 g/kg once daily); S-MCT: 1:1 beta-hydroxybutyrate salt: medium chain triglyceride oil (5 g/kg once daily). KE was more effective than BHB-S, S-MCT, or Control at preventing weight gain and maintaining a lower weight over the course of the 7-day study (p<0.01). Animals were provided ad libitum access to standard rodent chow. KE-treated animals were unique in that they self-restricted calories. This unintentional and surprising calorie restriction may have aided in the weight loss and weight maintenance effect of the KE.

FIG. 3 depicts results of a chronic feeding trial in rats. SD: standard rodent chow (fed ad libitum); LKE: low-dose R,S 1,3-butanediol diacetoacetate (approx. 5 g/kg/day in food); HKE: high-dose R,S 1,3-butanediol diacetoacetate (approx. 25 g/kg/day in food); BHB-S: beta-hydroxybutyrate salt (approx. 25 g/kg/day in food); S-MCT: 1:1 beta-hydroxybutyrate salt: medium chain triglyceride oil (approx. 25 g/kg/day). KE was more effective than BHB-S or S-MCT at preventing weight gain and maintaining a lower weight over the course of the 15-week study.

FIG. 5A illustrates that KE induced a quicker reduction in bodyweight. These reductions in bodyweight were at lower percentages of the ketogenic agent within the food. Additionally, KE animals reach target weight loss at much LOWER % of ketogenic agent integrated into the diet. FIG. 5B depicts KE group demonstrated greater effectiveness for weight loss compared to and all the other agents studied by assessing weight loss as a ratio to caloric intake/day across groups. In FIG. 5B, KE group was significantly more potent at inducing weight loss when divided by total caloric intake than the BHB, BHB+MCT, and CR groups, indicating that weight loss achieved by BHB+MCT and BHB could be explained by caloric restriction alone, but KE appears to induce weight loss through caloric restriction independent mechanisms. Taken together, these results indicate that KE is a quicker and more potent weight loss agent than other ketogenic agents and caloric restriction via multiple calorie and calorie independent mechanisms.

DETAILED DESCRIPTION

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings: Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ingredient" includes mixtures of two or more such ingredients, reference to "the supplement" includes mixtures of two or more such supplements, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

By "reduce" or "decrease" is meant lowering of an event or characteristic (e.g., calorie intake). It is understood that this is typically in relation to some standard or expected value, in other words it is relative, but that it is not always necessary for the standard or relative value to be referred to. For example, "reduces calorie intake" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treat", "treatment", "treating", and the like refer to acting upon a condition (e.g., weight gain after weight loss) with an agent (e.g., ketogenic supplementation) to affect the condition by improving or altering it. The improvement or alteration may include an improvement in symptoms or an alteration in the physiologic pathways associated with the condition. The aforementioned terms cover one or more treatments of a condition in a subject (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms, such maintenance of weight loss, prevention of weight gain after weight loss, decreasing feed efficiency, increasing metabolic inefficiency, increasing energy expenditure and resetting metabolic set point.

The term "patient" preferably refers to a human in need of treatment for inducing weight loss, inducing fat loss, and/or maintaining weight or fat loss. However, the term "patient" can also refer to non-human animals, preferably mammals such as dogs, cats, horses, cows, pigs, sheep and non-human primates, among others, that are in need of treatment of for inducing weight loss, inducing fat loss, and/or maintaining weight or fat loss. The term "patient" is used interchangeably with the term "subject."

As used herein, the term "composition" is intended to encompass a product comprising the specified ingredients in the specified amounts, as well as any product which results, directly or indirectly, from combination of the specified ingredients in the specified amounts.

As used herein "beta-hydroxybutyrate," also known as βHB or BHB, is a carboxylic acid having the general formula $CH_3CHOHCH_2COOH$ which may be utilized by a patient's body as a fuel source during instances of low glucose levels in the patient and is considered a ketone body. In the present disclosure, salt variants of beta-hydroxybutyrate are disclosed.

"Ketosis" as used herein refers to a subject having blood ketone levels within the range of about 0.5 mmol/L and about 16 mmol/L. Ketone levels sustained above 0.5 mmol/L and ideally in the range of 1.0 to 3.0 mmol/L appear to offer the most therapeutic effects in humans. Ketosis may improve mitochondrial function, elevate Krebs cycle intermediates (e.g., succinate, fumarate), decrease ROS production, reduce inflammation, elevate adenosine, increase the activity of neurotrophic factors associated, and induce and maintain weight loss.

The term "administration" or "administering" is used to describe the process in which individual ketone esters, including R,S-1,3-butanediol acetoacetate diester, and butanediol, R,S-1,3-butanediol, beta-hydroxybutyrate salts and/or medium chain triglycerides in any combination are delivered to a subject. The composition can be administered in various ways including oral, intragastric, and parenteral (referring to intravenous and intra-arterial and other appropriate parenteral routes), among others. Each of these conditions can be readily treated using other administration routes of RS 1,3-butanediol acetoacetate diester, R,S 1,3 butanediol diacetoacetate, medium chain triglycerides, and/ or other ketone salts or supplementation, derivatives, or any combination thereof to treat or prevent a disease or condition.

Administration will often depend upon the amount of compound administered, the number of doses, and duration of regimen. In an embodiment, multiple doses of the agent are administered. The frequency of administration of the agent can vary depending on any of a variety of factors, such as timing between administrations and objectives of the supplementation, i.e., induction and maintenance of weight loss, prevention of weight gain after weight loss, increase in energy expenditure, decrease in feed efficacy, increase in metabolic insufficiency, and/or reset of metabolic set point. The duration of administration of the agent, e.g., the period of time over which the agent is administered, can vary, depending on any of a variety of factors, including patient response, desired effect, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

The term "therapeutically effective amount" as used herein describes concentrations or amounts of components such as agents which are effective for producing an intended result, including maintenance of weight loss, increase in energy expenditure, decrease in feed efficacy, increase in metabolic insufficiency, and/or reset of metabolic set point. Compositions according to the present invention may be used to effect a favorable change in weight, whether that change is an improvement, relieving to some extent one or more of the symptoms of the condition being treated, and/or that amount that will prevent, to some extent, one or more of the symptoms of the condition that the host being treated has or is at risk of developing (e.g., weight gain).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

Throughout this disclosure reference to a compound with stereocenters that does not specify a specific stereochemistry is meant to include specific reference to each enantiomer, diastereomer, mesocompound, and racemic and scalenic mixtures thereof.

Reference will now be made in detail to specific aspects of the disclosed materials, compounds, compositions, articles, and methods, examples of which are illustrated in the accompanying Examples and Figures.

Weight loss can be achieved, but nearly everyone fails at maintaining that loss long term, with failure rates of weight loss maintenance being as high as 95%. It was found herein that ketone diesters (e.g., R,S 1,3 butanediol diacetoacetate) is able to induce, and importantly, maintain moderate or severe weight loss even after cessation of agent administration. Additionally, ketone diesters are uniquely able to induce superior adaptations above other forms of dietary meals and ketogenic supplements. Ketone diesters—and R,S 1,3 butanediol diacetoacetate in particular—provide a unique weight loss, fat loss and weight loss maintenance compound that is capable of promoting induction and more importantly maintenance of weight loss through a number of mechanisms.

Compositions

Disclosed herein are compositions for inducing weight loss, fat loss and maintaining the weight loss, attenuating weight gain, suppressing appetite or reducing calorie intake, decreasing feed efficiency, increasing metabolic inefficiency, increasing energy expenditure, and/or resetting metabolic set point. The disclosed compositions can comprise a ketogenic supplement in a pharmaceutically acceptable carrier. The amount of ketogenic supplement in the disclosed compositions can be from 1% to 99% by weight of the disclosed compositions, e.g., the ketogenic supplement can be from 1, 5, 10, 15, 20, 25, 30, 35, 40, 45, 50, 55, 60, 65, 70, 75, 80, 85, 90, 95, or 99% of the composition by weight, where any of the stated values can form an upper or lower endpoint of a range. Likewise the pharmaceutically acceptable carrier can be from 1% to 99% by weight of the disclosed compositions, e.g., the pharmaceutically acceptable carrier can be from 1, 5, 10, 15, 20, 25, 30, 35, 40, 45, 50, 55, 60, 65, 70, 75, 80, 85, 90, 95, or 99% of the composition by weight, where any of the stated values can form an upper or lower endpoint of a range. In specific examples, the ketogenic supplement is 1,3-butanediol acetoacetate diester. In a specific example, the ketogenic supplement is R,S 1,3-butanediol diacetoacetate or a derivative thereof.

The amount of these ketogenic supplement that can be present can be at least 0.001 g, e.g., from 0.001 g to 300 g, e.g., 0.001, 0.005. 0.01. 0.05, 0.1, 0.5, 1, 10, 20, 30, 40, 50, 60, 70, 80, 90, or 100 g, 200 g, 300 g where any of the stated values can form an upper or lower endpoint of a range. Further, the amount of the ketogenic supplement in the disclosed compositions can be an amount sufficient to provide from 0.5 g to 300 g, from 1 g to 40 g, from 5 g to 30 g, or from 10 g to 20 g of ketogenic supplement to a patient. In other examples, the ketogenic supplement can be present in the composition at 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, or 300 g. Alternatively, the ketogenic supplement can be present in the composition in an amount sufficient to provide from 0.001 g to 20 g per kg of bodyweight, or from 5 g to 10 g per kg of bodyweight. In other examples, the ketogenic supplement can be present in the composition at 0.001 mL, 0.005 mL, 0.01 mL, 0.05 mL, 0.1 mL, 0.5 mL, 1 ml, 2 mL, 4 mL, 5 mL, 6 mL, 7 mL, 8 mL, 9 mL, 10 ml, 11 ml, 12 mL, 13 mL, 14 mL, 15 mL, 17 mL, 19 mL, 20 mL, 22 mL, 24 mL, 26 mL, 28 mL, 30 mL, 32 mL, 34 mL, 36 mL, 38 mL, 40 mL, 42 mL, 44 mL, 46 mL, 48 mL, 50 mL, 52 mL, 54 mL, 56 mL, 58 mL, 60 mL, 62 mL, 64 mL, 66 mL, 68 mL, 70 mL, 72 mL, 74 mL, 76 mL, 78 mL, 80 mL, 82 mL, 84 mL. 86 mL, 88 mL, 90 mL, 92 mL, 94 mL, 96 ml, 98 mL, or 100 mL, per kg bodyweight.

In specific examples, the composition does not contain a beta-hydroxybutyrate, a monoester of beta-hydroxybutyrate, or glycerol.

In other examples, the ketogenic supplement can comprise one or more compounds chosen from acetoacetate, 1,3-butanediol, 1,3-butanediol acetoacetate monoester, 1,3-butanediol acetoacetate diester, or any combination thereof. In specific examples, the ketogenic supplement is R,S-1,3-butanediol acetoacetate diester combined with R,S-1,3-butandiol.

In further examples, the ketogenic supplement further includes a medium chain triglyceride (MCTs), monoglycerides, diglycerides, alkyl esters, or free acids thereof. Nonlimiting examples and sources of the medium chain triglycerides include coconut oil, coconut milk powder, fractionated coconut oil, palm oil, palm kernel oil, triglycerides of caproic acid, triglycerides of caprylic acid, triglycerides of capric acid, and any combination thereof. The amount of these MCTs in the disclosed compositions can be from 0.001 g to 300 g, e.g., 0.001, 0.5, 1, 10, 20, 30, 40, 50, 60, 70, 80, 90, 100 g, 200 g, or 300 g where any of the stated values can form an upper or lower endpoint of a range. Further, the amount of MCTs in the disclosed compositions can be an amount sufficient to provide from 0.001 g to 300 g, from 1 g to 40 g, from 5 g to 30 g, or from 10 g to 20 g of MCT to a patient. In other examples, the MCTs can be present in the composition at 0.001, 0.005. 0.01. 0.05, 0.1, 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, or 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, or 300 g. Alternatively, the MCTs can be present in the composition in an amount sufficient to provide from 0.001 g to 20 g per kg of patient, or from 5 g to 10 g per kg of patient.

The ketogenic supplement disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the ketogenic supplement is combined with a pharmaceutically acceptable carrier in order to facilitate effective administration of the compound. The resulting compositions used can also be in a variety of forms. These include, for example, solid, semi-solid, and liquid dosage forms, such as tablets, pills, powders, liquid solutions or suspension, suppositories, injectable and infusible solutions, topical application compositions, and sprays. The preferred form depends on the intended mode of administration and therapeutic application. The compositions also include conventional pharmaceutically-acceptable carriers, which are known to those skilled in the art. Examples of carriers for use with the disclosed compositions compounds include water, milk, juice, ethanol, dimethyl sulfoxide, glycerol, alumina, starch, saline, and equivalent carriers.

In a specific example, the disclosed compositions comprise a ketogenic supplement (e.g., R,S 1,3-butanediol acetoacetate diester, MCTs, or combinations thereof) and a liquid pharmaceutical carrier, such as water, fruit juice, or milk.

The compositions disclosed herein can further comprises additional vitamins (e.g., Vitamin A, Vitamin B6, Vitamin B12, Vitamin C, Vitamin D, Vitamin E) and/or minerals (e.g., potassium, calcium, magnesium, chromium, selenium), proteins, essential amino acids, branch chain amino acids, amino acids, or derivatives, which can be co-administered with ketone supplementation.

In further examples, disclosed herein are foodstuffs that comprise a ketogenic supplement. For example, disclosed are snack foods, nutritional bars, protein bars, beverages that comprise a ketogenic supplement (e.g., R,S 1,3-butanediol acetoacetate diester, MCTs, or combinations thereof).

Ketogenic supplement can be combined with protein, amino acids, or derivative of these combinations.

In further examples, the composition can include one or more of a medium chain triglyceride, beta-hydroxybutyrate, or a salt of beta-hydroxybutyrate. Nonlimiting examples of the beta-hydroxybutyrate salts include sodium beta-hydroxybutyrate, arginine beta-hydroxybutyrate, potassium beta-hydroxybutyrate, calcium beta-hydroxybutyrate, magnesium beta-hydroxybutyrate, lithium beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, or a combination of salts. Nonlimiting examples of combinations of beta-hydroxybutyrate salts include sodium beta-hydroxybutyrate and arginine beta-hydroxybutyrate, or beta-hydroxy butyrate sodium salt and beta-hydroxy butyrate potassium salt. These components can be used to maintain weight and/or fat loss. They can be combined with the ketogenic supplements disclosed herein or be a separate composition.

Methods

Also disclosed herein are methods of inducing weight loss, inducing fat loss, maintaining the weight and fat loss, attenuating weight gain, suppressing appetite or reducing calorie intake, decreasing feed efficiency, increasing metabolic inefficiency, increasing energy expenditure, and/or resetting metabolic set point in a subject comprising administering a therapeutically effective amount of a ketogenic supplement. Further, disclosed are methods of improving thermogenesis or energy expenditure by administering to a patient a therapeutically effective amount of a ketogenic supplement. In still further examples, disclosed are methods of treating adipose tissue wasting by administering to a patient a therapeutically effective amount of a ketogenic supplement. In some examples, the patient can be obese, one who is preparing for or has undergone surgery for weight loss (e.g., bariatric surgery), one who has previously undergone a weight loss program, or one who has had their weight cycled. In other examples, the patient can have Type-2 Diabetes. In yet further examples, the patient can have low thyroid hormone (hypothyroid). In other examples, the patient can have a metabolic syndrome. The patient can also be one who has maintained a low caloric intake for extended periods or who have reduced energy expenditure.

The ketogenic supplement can be 1,3-butanediol acetoacetate diester, e.g., R,S-1,3-butanediol diacetoacetate or a derivative thereof. The ketogenic supplement can be acetoacetate, 1,3-butanediol, 1,3-butanediol acetoacetate monoester, 1,3-butanediol acetoacetate diester, or any combination thereof. In specific examples the ketogenic supplement is R,S-1,3-butanediol acetoacetate diester combined with R,S-1,3-butandiol. The ketogenic supplement can be administered in any amount, e.g., at least 0.001 g. For example, the ketogenic supplement can be administered in an amount from 0.001 g to 300 g, e.g., 0.001 g, e.g., from 0.001 g to 300 g, e.g., 0.001, 0.005. 0.01. 0.05, 0.1, 0.5, 1, 10, 20, 30, 40, 50, 60, 70, 80, 90, 100, 200, or 300 g, where any of the stated values can form an upper or lower endpoint of a range. Further, the amount of ketogenic supplement in the disclosed compositions can be administered in an amount sufficient to provide from 0.001 g to 300 g, from 1 g to 40 g, from 5 g to 30 g, or from 10 g to 20 g of ketogenic supplement to a patient. In other examples, the ketogenic supplement can be administered at 0.001 g, 0.005 g, 0.01 g, 0.05 g, 0.1 g, 0.5 g, 1 g, 2 g, 4 g, 5 g, 6 g, 7 g, 8 g, 9 g, 10 g, 11 g, 12 g, 13 g, 14 g. 15 g, 17 g, 19 g, 20 g, 22 g, 24 g, 26 g. 28 g, 30 g, 32 g, 34 g, 36 g, 38 g, 40 g, 42 g, 44 g, 46 g, 48 g, 50 g, 52 g, 54 g, 56 g, 58 g, 60 g, 62 g, 64 g, 66 g, 68 g, 70 g, 72 g, 74 g, 76 g, 78 g. 80 g, 82 g, 84 g, 86 g, 88 g, 90 g, 92 g. 94 g, 96 g, 98 g, 100 g, 200 g, or 300 g. Alternatively, the ketogenic supplement can be administered in the composition in an amount sufficient to provide from 0.001 g to 20 g per kg of patient, or from 5 g to 10 g per kg of patient. In other examples, the ketogenic supplement can be administered at 0.001 mL, 0.005 mL, 0.01 mL, 0.05 mL, 0.1 mL, 0.5 mL, 1 mL, 2 mL, 4 mL, 5 mL, 6 mL, 7 mL, 8 mL, 9 mL, 10 mL, 11 mL, 12 mL, 13 mL, 14 mL, 15 mL, 17 mL, 19 mL, 20 mL, 22 mL, 24 mL, 26 mL, 28 mL, 30 mL, 32 mL, 34 mL, 36 mL, 38 mL, 40 mL, 42 mL, 44 mL, 46 mL, 48 mL, 50 mL, 52 ml, 54 mL, 56 mL, 58 mL, 60 mL, 62 mL, 64 mL, 66 mL, 68 ml, 70 mL, 72 mL, 74 ml, 76 mL, 78 ml, 80 mL, 82 mL, 84 mL, 86 mL, 88 mL, 90 ml, 92 mL, 94 mL, 96 mL, 98 mL, or 100 mL, per kg bodyweight.

In the disclosed methods the ketogenic supplement can be administered in an amount sufficient to provide a circulating level of hydroxybutyrate and acetoacetate in the blood from 0.1 to 20 mM, preferably 0.5 to 10 mM and optimally from 1 to 8 mM for example from 2 to 5 mM, wherein at least one dose comprises a ketogenic supplement in an amount of at least 0.1 g/kg bodyweight of the patient per dose and preferably from 0.3 to 1.5 g/kg for example at least 0.3 to 0.75 g/kg bodyweight.

In the disclosed methods, the methods can further comprise the administration of a MCTs. Non-limiting examples and sources of the MCTs include coconut oil, coconut milk powder, fractionated coconut oil, palm oil, palm kernel oil, triglycerides of caproic acid, triglycerides of caprylic acid, triglycerides of capric acid, and any combination thereof. The amount of these MCTs that can be administered can be from 0.001 g to 300 g, e.g., 0.001 g, e.g., from 0.001 g to 300 g, e.g., 0.001, 0.005. 0.01. 0.05, 0.1, 0.5, 1, 10, 20, 30, 40, 50, 60, 70, 80, 90, or 100 g, 200 g, 300 g, where any of the stated values can form an upper or lower endpoint of a range. Further, the amount of MCTs that can be administered can be an amount sufficient to provide from 0.5 g to 50 g, from 1 g to 40 g, from 5 g to 30 g, or from 10 g to 20 g of MCT to a patient. In other examples, the MCTs can be administered at 0.001, 0.005. 0.01. 0.05, 0.1, 0.5 g, 1 g, 2 g, 4 g, 5 g, 6 g, 7 g, 8 g, 9 g, 10 g, 11 g, 12 g, 13 g, 14 g, 15 g, 17 g, 19 g, 20 g, 22 g, 24 g, 26 g, 28 g, 30 g, 32 g, 34 g, 36 g, 38 g, 40 g, 42 g, 44 g, 46 g, 48 g, or 50 g, 52 g, 54 g, 56 g, 58 g, 60 g, 62 g, 64 g, 66 g, 68 g, 70 g, 72 g, 74 g, 76 g, 78 g, 80 g, 82 g, 84 g, 86 g, 88 g, 90 g, 92 g, 94 g, 96 g, 98 g, 100 g, 200 g, 300 g. Alternatively, the MCTs can be administered at from 1 g to 20 g per kg of patient, or from 5 g to 10 g per kg of patient.

In the disclosed methods, the ketogenic supplement can be administered on a regimen of 1 to 6 times per day, such as once or twice per day. This dosing regimen can be adjusted to provide the optimal therapeutic response. Ketogenic supplement can be administered prior, during or post to disease or disorder initiation, or independent of disease or disorder state. Ketogenic supplement can be administered topically. It can be co-administered with glucose, fructose, sucralose, galactose or derivative thereof, or protein, essential amino acids, branch chain amino acids, amino acids, derivatives thereof. Ketogenic supplement can be administered during fasting, non-fasting, with a meal, prior to a meal, or following a meal.

In further examples, the ketogenic supplement can be administered with one or more of a medium chain triglyceride, beta-hydroxybutyrate, or a salt of beta-hydroxybutyrate. Nonlimiting examples of the beta-hydroxybutyrate salts include sodium beta-hydroxybutyrate, arginine beta-hydroxybutyrate, potassium beta-hydroxybutyrate, calcium beta-hydroxybutyrate, magnesium beta-hydroxybutyrate, lithium beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, or a combination of salts. Nonlimiting examples of combinations of beta-hydroxybutyrate salts include sodium beta-hydroxybutyrate and arginine beta-hydroxybutyrate, or beta-hydroxy butyrate sodium salt and beta-hydroxy butyrate potassium salt. These components can be used to maintain weight and/or fat loss. They can be administered as part of a combined composition with the ketogenic supplements disclosed herein or be administered as a separate composition before, current, or after administration of the ketogenic supplement.

In any of the disclosed methods herein the ketogenic supplement can be administered with a standard diet, e.g., without restrictions as to glucose intake.

In other examples, the ketogenic supplement is administered acutely, e.g., oral. In other examples, the ketogenic supplement is administered chronically.

In further examples, the ketone diester can be administered to a patient that has lost weight, e.g., within the past week or month.

In any of the disclosed methods, the ketogenic supplement can be administered prior to disease onset, during the disease, and/or in a post disease state.

Examples

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Study 1

R,S 1,3-butanediol diacetoacetate (KE; 10-20% by weight mixed into standard chow) was administered to VM/Dk mice at for both males and females for 28 days. Standard rodent chow (SD) and ketogenic diet chow (KD) were administered to other VM/Dk mice ad libitum for comparison.

Mice ingesting the ketone diester lost significantly more bodyweight and white adipose tissue while maintaining that weight loss for 28 days, as compared to VM/Dk animals consuming SD or KD. Additionally, chronically administering KE into food was able to induce reductions in white adipose tissue compared to SD or KD alone. This data suggests that administration of R,S 1,3 butanediol diacetoacetate is a more effective weight loss, fat loss and weight loss maintenance tool than other dietary regimens ad libitum even when calories are equivalent between dietary regimens, indicating decreased feed efficiency, increased metabolic inefficiency, and potentially increases in energy expenditure and resetting of metabolic set point. See FIGS. 1A-1H.

Study 2

Figure 6:
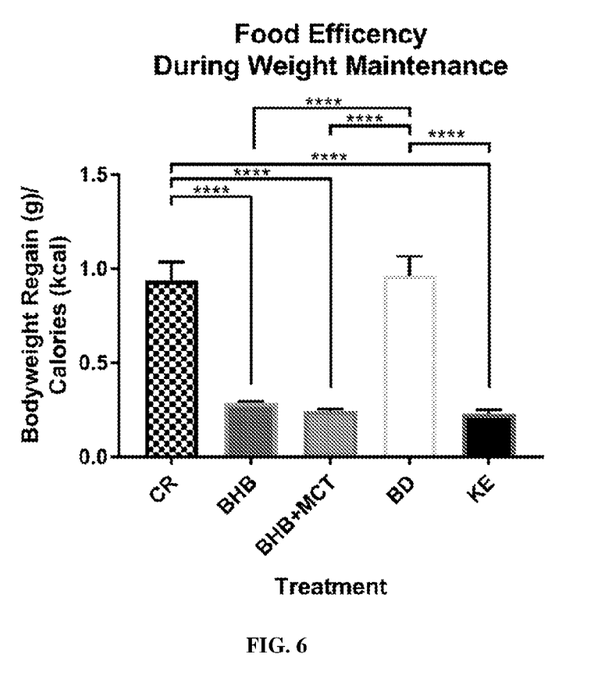
FIG. 6 depicts food efficiency during weight loss maintenance by calculating bodyweight regain proportional to calories consumed. Treatments: Standard Diet ad-Libitum (SD-AL); Standard Diet Caloric Restriction (CR); Beta-Hydroxybutyrate (BHB); Beta-Hydroxybutyrate+Medium Chain Triglycerides (BHB+MCT); Butanediol (BD); R,S 1,3-Butanediol Acetoacetate Diester (KE). Data indicate that upon cessation of ketogenic supplement ingestion or caloric restriction, KE, BHB+MCT, and BHB had lingering effects on food efficiency and weight loss maintenance compared to either caloric restriction and butanediol alone, illustrating mechanisms supporting weight loss maintenance in BHB, BHB+MCT, and KE.

R,S 1,3-butanediol diacetoacetate (KE; 10-15% by weight mixed into standard chow), 1,3 Butanediol (BD 20-45% by weight), BHB-salt (15-75% by weight), BHB-salt+MCT (30-75% by weight) are administered to C57BL/6J mice. Administration of KE, BD, BHB-salt, and BHB-salt+MCT is expected to result in a weight loss of approximately 10-30%. Animals are returned to standard rodent chow ad libitum and the KE group is expected to be able to maintain weight loss more effectively compared to BD, BHB-salt, and BHB-salt+MCT for several weeks until euthanasia, even after administration of the agent ceases. This data suggests that R,S 1,3 butanediol diacetoacetate can induce weight loss and that weight loss is maintained following removal of intervention better than other ketogenic agents. It may indicate that the agent increases energy expenditure, decreases feed efficiency, increases metabolic inefficiency and resets metabolic set point long term, even after cessation of compound intake, providing an effective long-term weight loss maintenance tool. BHB and BHB+MCT also helped maintain weight loss post cessation of agent administration indicating that BHB and BHB+MCT also will assist in weight loss maintenance through increased feed inefficiency (FIG. 6).

Study 3

Figure 1A:
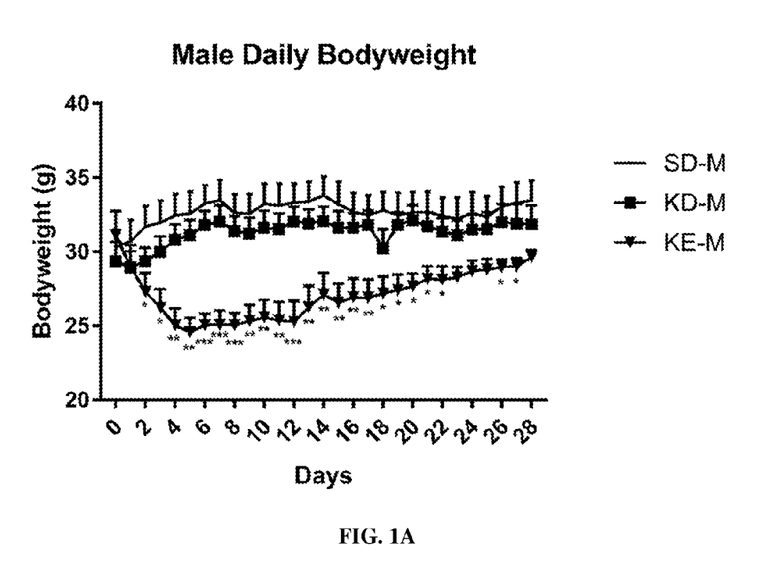
FIGS. 1A-1H depict results of a chronic ad libitum feeding trial of male and female mice (Standard Diet Male (n=7)=SD-M; Ketogenic Diet Male (n=7)=KD-M; R/S 1,3 Butanediol Acetoacetate Diester (n=4)=KE-M; Standard Diet Female (n=7)=SD-F; Ketogenic Diet Female (n=6) =KD-F; R/S 1,3 Butanediol Acetoacetate Diester Female (n=4)=KE-F). It can be seen that R,S 1,3-butanediol diacetoacetate (KE) induced and maintained long-term weight loss in VM/Dk mice compared to standard rodent chow (SD) and ketogenic diet chow (KD). Additionally, chronically administering KE into food was able to induce reductions in white adipose tissue compared to SD or KD alone.
Figure 1B:
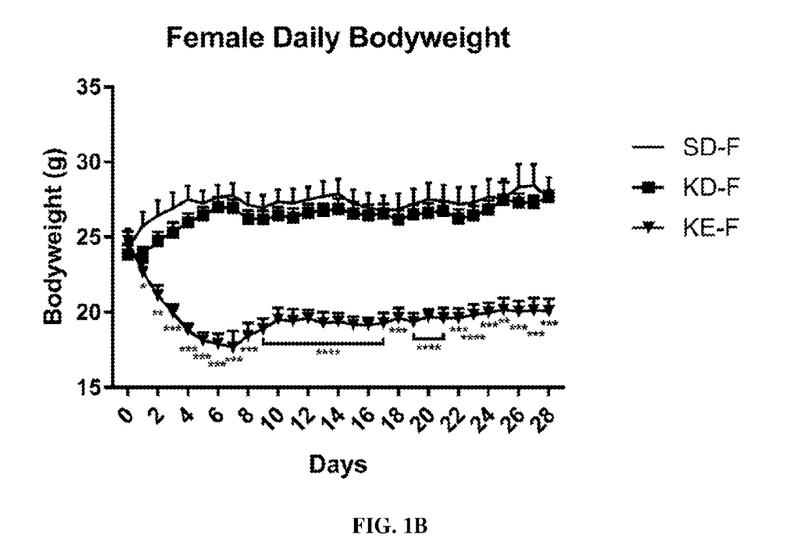
Figure 1C:
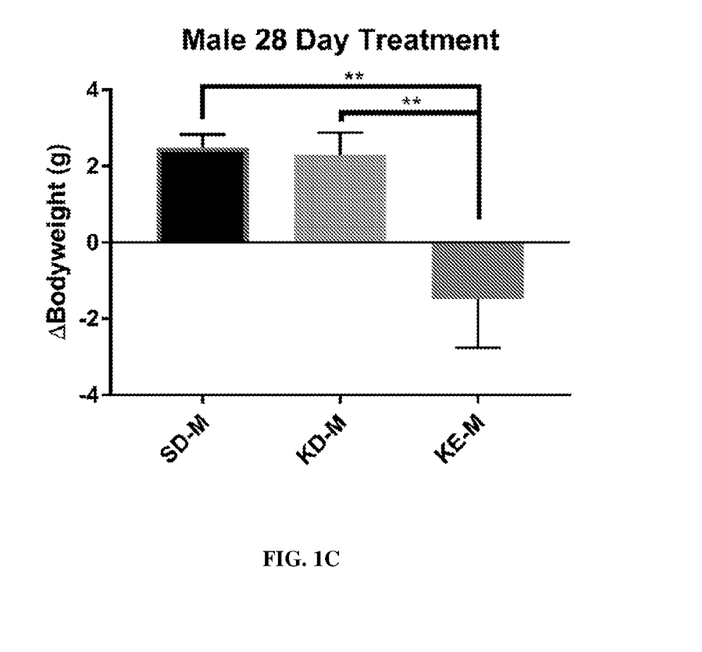
Figure 1D:
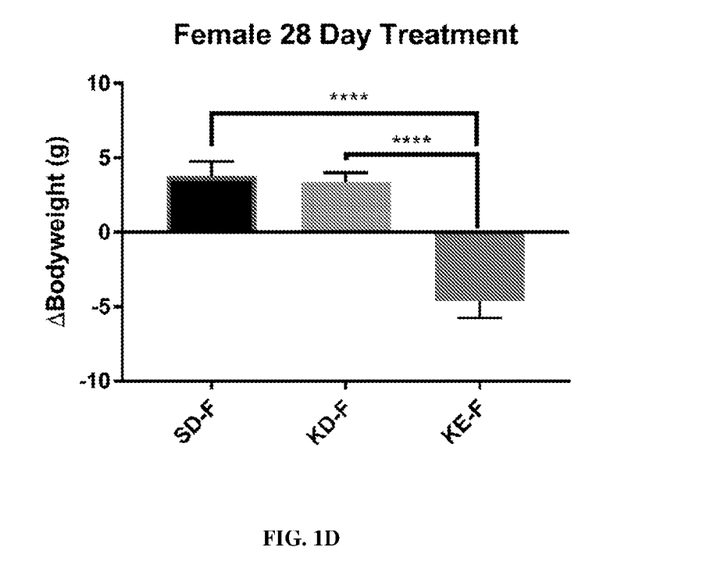
Figure 1E:
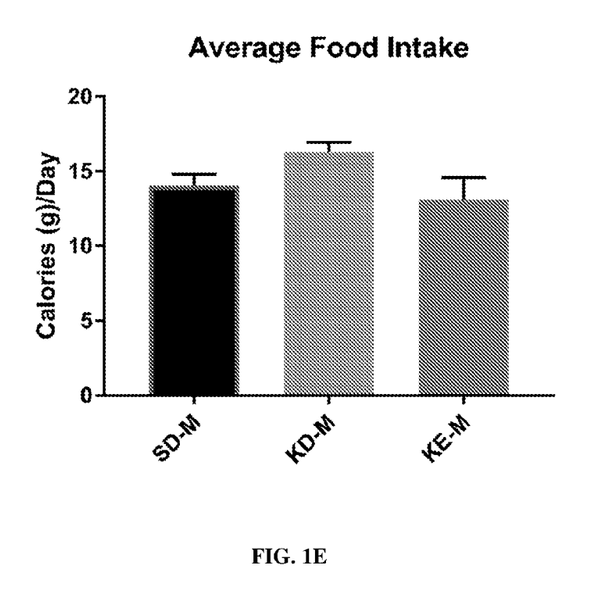
Figure 1F:
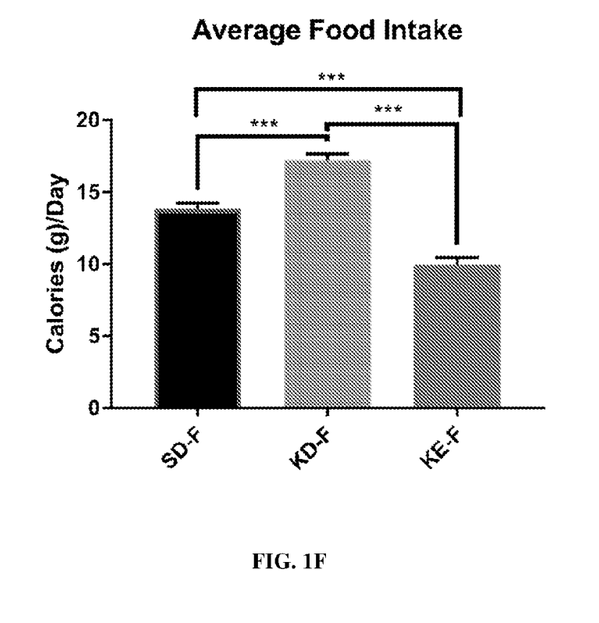
Figure 1G:
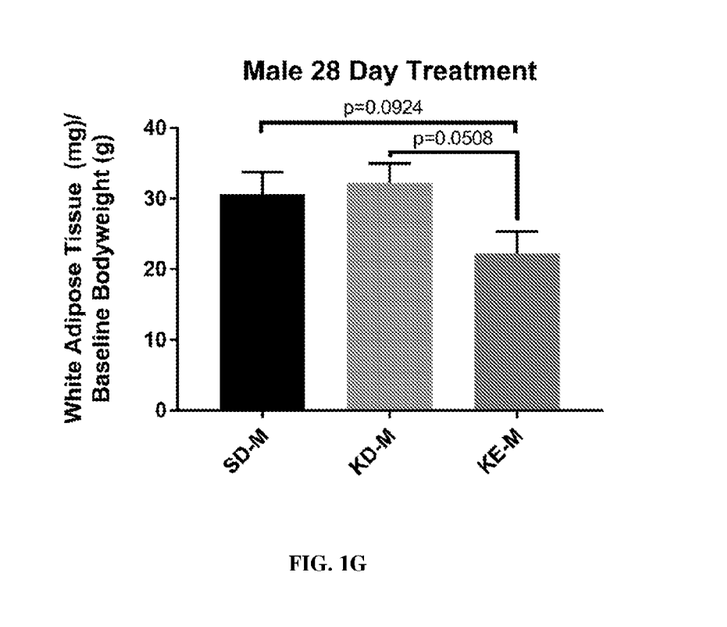
Figure 1H:
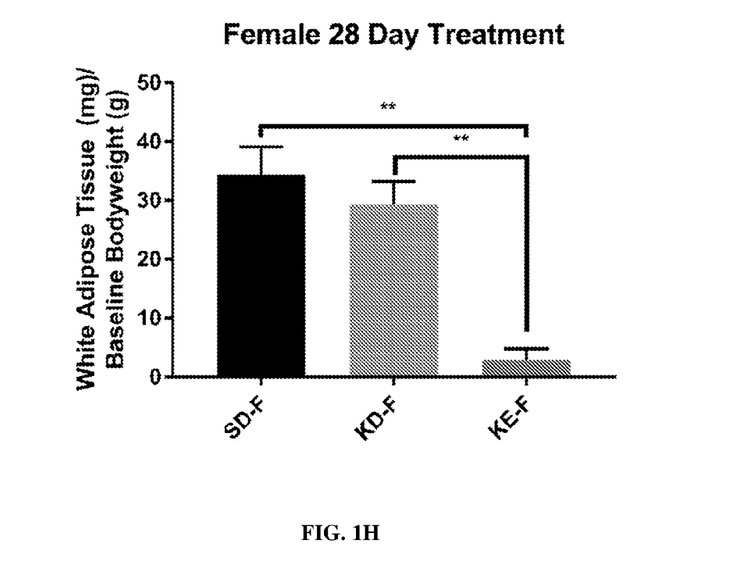
Figure 2A:
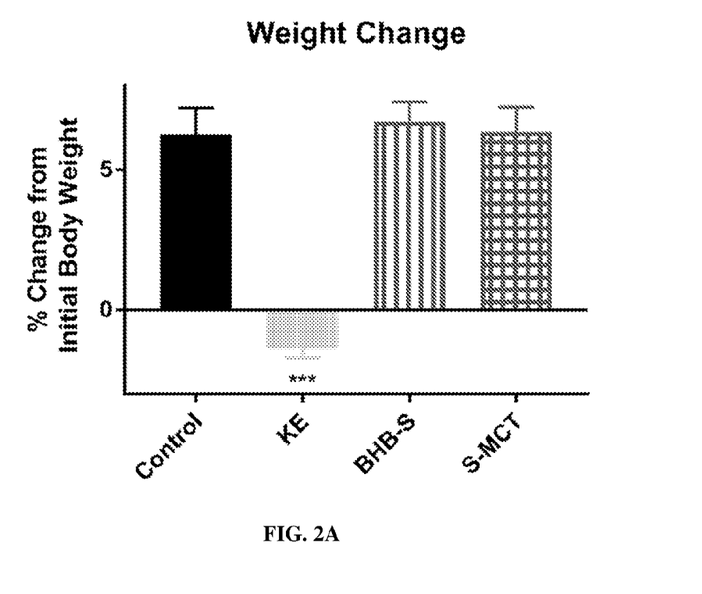
Figure 2B:
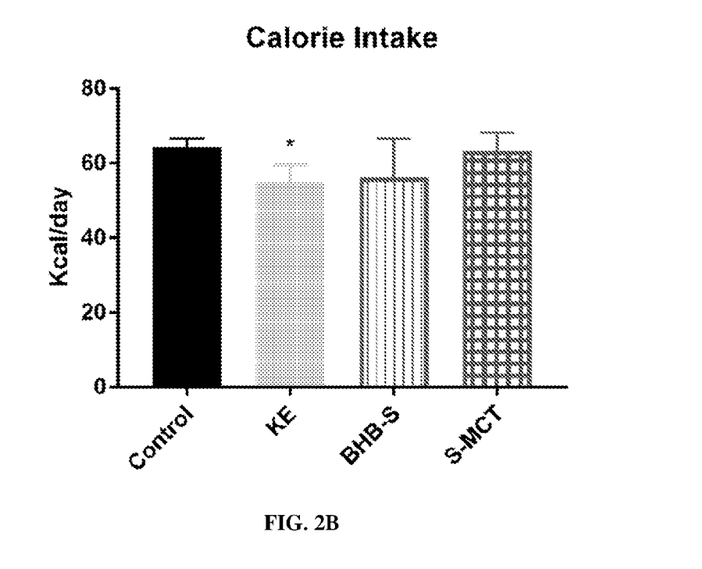

R,S 1,3 butanediol diacetoacetate (KE) was administered to Sprague Dawley Rats by oral gavage (at 5 mL/kg, which may translate to about 300-700 mg/kg for a human). Water, BHB-salt, or BHB-salt+MCT mixture was administered to other Sprague Dawley Rats for comparison. Animals were provided ad libitum access to standard rodent chow. Administration of KE resulted in significantly lower bodyweight compared to animals administered water, BHB-salt, or BHB-salt+MCT mixture. Additionally, it can be seen that KE was more effective than BHB-S or S-MCT at preventing weight gain and maintaining a lower weight over the course of the 7-day study. It was further seen that animals administered KE self-restricted calories. See FIGS. 2A-2B.

Study 4

Figure 3:
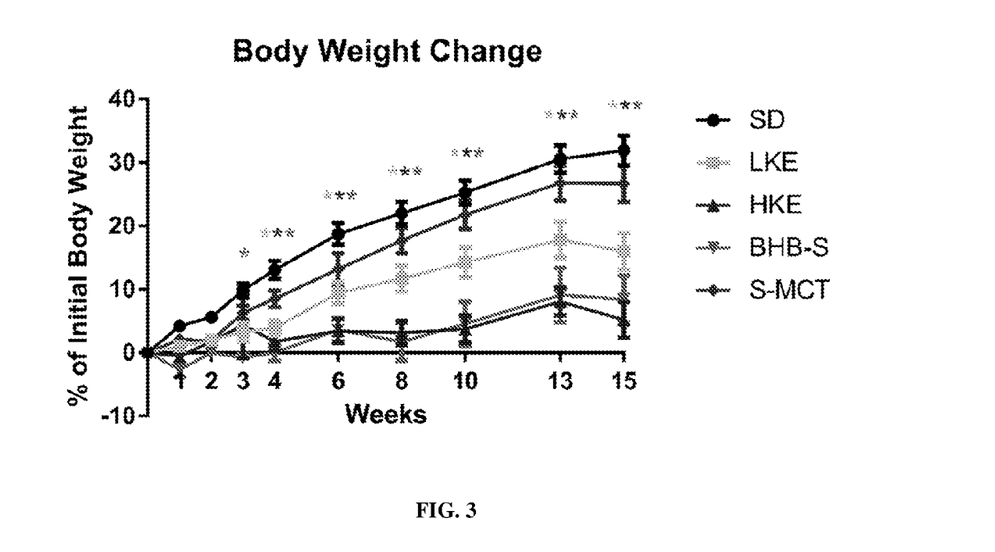
Figure 4A:
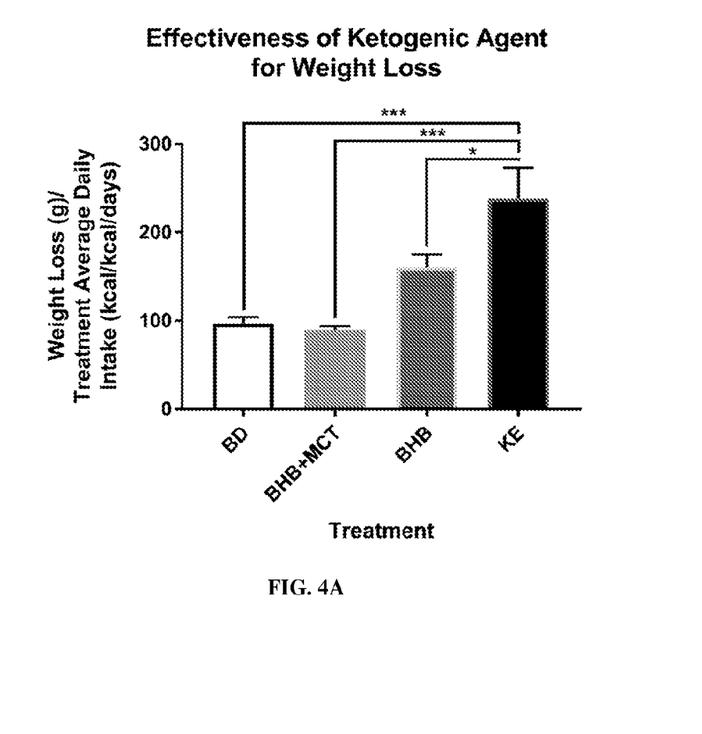
FIGS. 4A-4B depict results of weight loss induced by various ketogenic agents against regular SD caloric restriction, illustrating the effectiveness of various ketogenic agents for inducing weight loss. Treatments: Beta-Hydroxybutyrate (BHB); Beta-Hydroxybutyrate+Medium Chain Triglycerides (BHB+MCT); Butanediol (BD); R,S 1,3-Butanediol Acetoacetate Diester (KE). Data indicate that R,S 1,3 Butanediol Acetoacetate diester is a superior weight loss agent per total average daily intake compared to butanediol, BHB+MCT, and BHB.
Figure 4B:
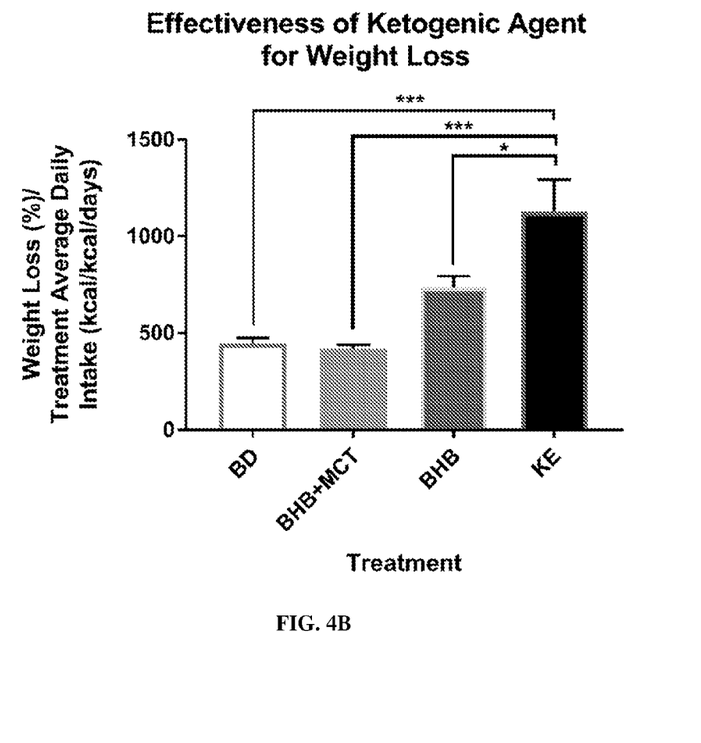
Figure 5A:
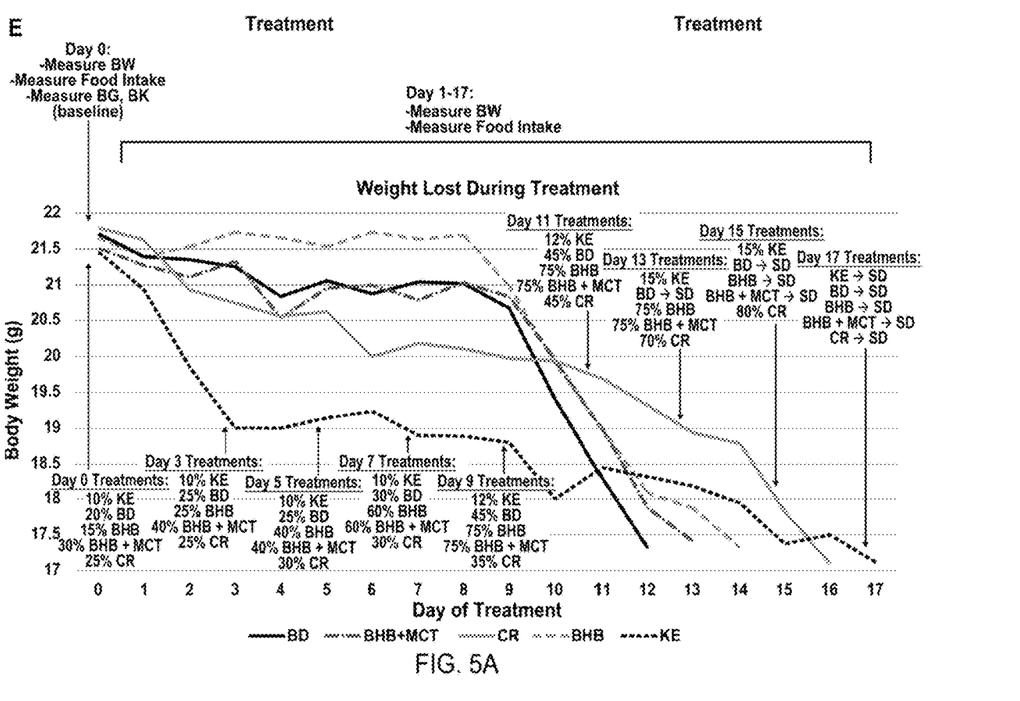
FIGS. 5A-5B depict treatment timeline of weight loss study utilizing various ketogenic agents against SD caloric restriction, as well as evaluation of weight loss potency of each ketogenic agent. Treatments: Standard Diet ad-Libitum (SD-AL); Standard Diet Caloric Restriction (CR); Beta-Hydroxybutyrate (BHB); Beta-Hydroxybutyrate+Medium Chain Triglycerides (BHB+MCT); Butanediol (BD); R,S 1,3-Butanediol Acetoacetate Diester (KE).
Figure 5B:
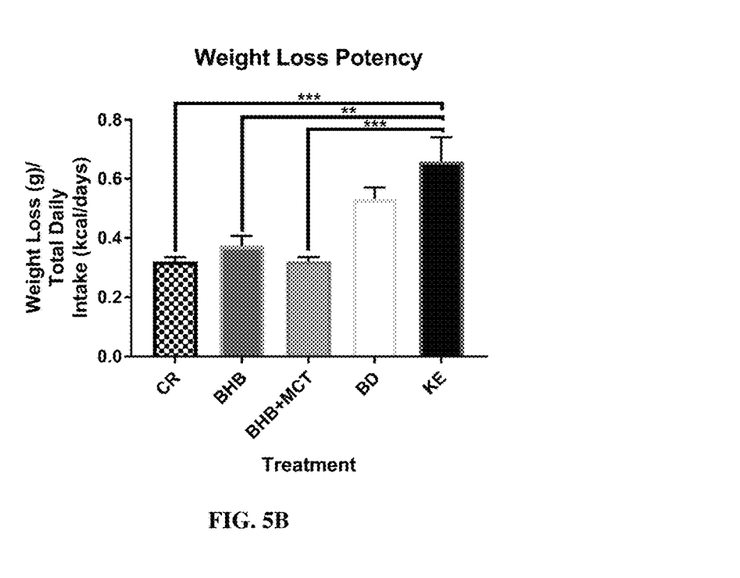

Additionally, chronic administration (15 weeks) of R,S 1,3 butanediol diacetoacetate in Sprague Dawley Rats by food incorporation (25 g/kg/d) resulted in significantly lower bodyweight compared to animals administered standard diet alone or BHB-salt+MCT mixture. It was further seen that KE was more effective than BHB-S or S-MCT at preventing weight gain and maintaining a lower weight over the course of the 15-week study. Consequently, this data suggests that R,S 1,3-butanediol diacetoacetate is uniquely able to induce greater weight loss and promote weight loss maintenance compared to other exogenous ketogenic agents. See FIG. 3 and Table 1.

TABLE 1

| Approximate caloric intake compared to controls following adaptation to diet (weeks 13-15) | |
|---|---|
| LKE | +10% kcal |
| HKE | −7% kcal |
| BHB-S | −25% kcal |
| S-MCT | −8.8% kcal |

Study 5

C57BL/6J animals were obtained. Prior to experimental initiation, animals were randomly assigned to one (1) of five (5) groups: Caloric Restriction with standard diet (SD), Beta-hydroxybutyrate with SD (BHB), BHB+Medium Chain Triglycerides with SD (BHB+MCT), 1,3-Butanediol with SD (BD), and R,S 1,3 Butanediol Acetoacetate Diester with SD (KE). All animals initiated weight loss by either reducing the amount of calories consumed (CR group) or adding various % of ketogenic agents to induce weight loss. There was no difference in bodyweight across groups at baseline. All animals underwent weight loss until 20% weight loss was achieved. Upon reaching 20% weight loss, animals were switched back onto ad-libitum SD.

Calories intake, bodyweight, and kcal of ketogenic agent in diet were recorded daily. In order to calculate the effectiveness of each agent to induce weight loss, weight loss as both grams and % weight loss, was compared as a ratio to the amount of kcal from each ketogenic agent compared to total kcals consumed a day.

Weight loss. FIGS. 4A-4B & 5A-5B indicate that the KE was the most effective agent to induce weight loss compared to other ketogenic agents administered. The data shows that KE is superior per kcal used at inducing weight loss. This data also shows that KE induces more rapid weight loss and low quantities of the agent administered (potency).

Weight loss maintenance. FIG. 6A indicates that during weight loss and weight loss maintenance after cessation of agent ingestion, BHB, BHB+MCT, and KE were more effective at inducing inefficiencies in kcal consumed, indicating that BHB, BHB+MCT, and KE reduce the bodyweight gain from the calories consumed compared to BD or doing a CR diet. This, in turn, provides evidence that BHB, BHB+MCT, and KE help contribute to maintenance of weight loss after cessation of the ketogenic agent, by reducing food efficiency after weight loss was achieved and all ketogenic agents have been removed during the initial phase of weight maintenance. In other words, there appears to be lingering effects to ingestion of BHB, BHB+MCT, and KE that influences bodyweight regain after cessation of BHB, BHB+MCT, and KE, respectively. The data shows that BHB, BHB+MCT, and KE have similar effects for one biomarker of maintenance after the agents are removed.

When studies 1-4 are taken together, R,S 1,3-butanediol diacetoacetate provides a superior weight loss, fat loss and weight loss maintenance tool, and is superior to other ketogenic agents at attenuating weight gain, suppressing appetite or reducing calorie intake, decreasing feed efficiency, increasing metabolic inefficiency, increasing energy expenditure, and/or resetting metabolic set point tool compared to other dietary or supplemental regiments. Additionally, this is the first data to indicate that R,S 1,3-butanediol diacetoacetate, BHB-S, and BHB-salt+MCT help contribute to maintenance of weight loss after cessation of weight loss intervention by reducing food efficiency along with other weight homeostasis mechanisms post-weight intervention cessation. This is the first time any data has looked at the effectiveness BETWEEN ketogenic agents and their effectiveness at inducing weight loss. This is the first data to indicate that R,S 1,3-butanediol diacetoacetate, BHB-S, and BHB-salt+MCT assist in weight loss maintenance. This is the first data to indicate that R,S 1,3-butanediol diacetoacetate, BHB-S, and BHB-salt+MCT can assist with weight loss maintenance, over other weight loss strategies and ketone supplementation, even after cessation of weight loss intervention.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of inducing weight loss, inducing fat loss, and/or maintaining the weight or fat loss, comprising:
   administering a therapeutically effective amount of a composition comprising R,S 1,3-butanediol diacetoacetate diester and a pharmaceutically acceptable carrier, wherein the composition is a food with about 10-30% by weight R,S 1,3-butanediol diacetoacetate diester.

2. The method of claim 1, wherein the weight loss is maintained even after stopping administration of the composition.

3. The method of claim 1, wherein the composition further comprises one or more beta-hydroxybutyrate, beta-hydroxybutyrate salt, or medium chain triglycerides.

4. The method of claim 1, further comprising administering to the patient one or more beta-hydroxybutyrate, beta-hydroxybutyrate salt, or medium chain triglycerides.

5. The method of claim 1, wherein the R,S 1,3 butanediol acetoacetate diester is in an amount sufficient to maintain the weight or fat loss after cessation of administration of the composition.

6. The method of claim 1, wherein the patient is obese, one who is preparing for or has undergone surgery for weight loss, one who has previously undergone a weight loss program, one who has had their weight cycled, a type-2 diabetic, has low thyroid hormone, has a metabolic syndrome, maintained a low caloric intake for extended periods, or who have reduced energy expenditure.

7. The method of claim 1, wherein the food is a snack food, nutritional bar, protein bar, or beverage.

8. The method of claim 1, wherein the pharmaceutically acceptable carrier is a liquid pharmaceutical carrier comprising water, milk, or juice.

9. The method of claim 1, wherein the composition has from 0.5 to 300 g of R,S 1,3-butanediol diacetoacetate diester.

* * * * *